United States Patent [19]

Schubert et al.

[11] Patent Number: 5,128,298
[45] Date of Patent: Jul. 7, 1992

[54] POTASSIUM CARBONATE SUPPORTS AND CATALYSTS

[75] Inventors: Paula F. Schubert, Campbell, Calif.; Donald H. Kubicek, Bartlesville, Okla.

[73] Assignee: Phillips Petroleum Company, Bartlesville, Okla.

[21] Appl. No.: 726,428

[22] Filed: Jul. 5, 1991

[51] Int. Cl.⁵ .................. B01J 27/232; B01J 37/04; B01J 23/04
[52] U.S. Cl. .................................................. 502/174
[58] Field of Search .......................................... 502/174

[56] References Cited

U.S. PATENT DOCUMENTS 3,989,645  11/1976  Long ................................ 252/462
4,162,285   7/1979  Tanabashi ......................... 264/66
4,172,809  10/1979  Triki .............................. 252/455 R
4,810,688   3/1989  Ewert et al. ...................... 502/174

Primary Examiner—W. J. Shine
Assistant Examiner—Douglas J. McGinty
Attorney, Agent, or Firm—Lynda S. Jolly

[57] ABSTRACT

Catalyst supports, catalyst systems, methods for the preparation thereof, and dimerization process therewith are provided. Catalyst supports are prepared from an alkali metal carbonate, and methanol or a methanol/higher alcohol mixture, and optionally at least one carbonaceous compound. Catalyst systems comprise at least one elemental alkali metal deposited on the catalyst support. Optionally, the catalyst system further comprises at least one promoter.

16 Claims, No Drawings

POTASSIUM CARBONATE SUPPORTS AND CATALYSTS

BACKGROUND OF THE INVENTION

This invention relates to alkali metal carbonate supported alkali metal catalysts.

It is known in the art to employ alkali metal carbonate supported alkali metal catalysts for such conversions as propylene dimerization. It is also known in the art to prepare metal carbonate catalyst supports by making a thick paste in water or water and an alcohol and eventually forming a pelletized, tabletted, or granular support. The support prepared in such a manner subsequently can be washed or treated with alcohol. Alkali metal carbonate catalyst supports prepared from a water-based or water/alcohol-based paste are difficult to process because the alkali metal carbonate to water ratio must be closely controlled or the paste can have the wrong consistency. Thus, it can be difficult to process and easily form a useable catalyst support. Furthermore, alkali metal carbonate catalyst supports prepared from water and alcohol are not very porous and, thus, preparation of a catalyst system by impregnation of an elemental alkali metal onto the support can be difficult.

SUMMARY OF THE INVENTION

It is an object of this invention to provide a process to easily prepare an alkali metal carbonate catalyst support.

It is a further object of this invention to provide an easily processed alkali metal carbonate catalyst support.

It is yet another object of this invention to provide a method to prepare an improved alkali metal carbonate supported elemental alkali metal catalyst system.

It is yet a further object of this invention ot provide an improved catalyst system for the dimerization of olefins.

It is yet another object of this invention to provide an improved process for the dimerization of olefins.

In accordance with the present invention, an alkali metal carbonate catalyst support is prepared from a thick paste comprising alkali metal carbonate, methanol, and optionally, a higher alcohol. The resultant thick paste is formed into a particulate product and calcined to give a durable, porous catalyst support.

In accordance with another embodiment of this invention, the alkali metal carbonate catalyst support can be contacted with an elemental alkali metal to form a catalyst system which can be useful to dimerize olefins.

DESCRIPTION OF THE INVENTION

The present invention provides a process to prepare a catalyst support which comprise the steps of forming a thick paste comprising an alkali metal carbonate, methanol, and, optionally, a higher alcohol; forming a particulate product from said paste; and clacining said particulate product. The particulate product can be formed by grinding and seiving prior to clacining, or it can be formed into an extrudate, pellets, tablets, pills, or any other granular form prior to calcining.

In accordance with one embodiment of the invention, the thick paste comprising an alkali metal carbonate, methanol, and, optionally, a higher alcohol, can further comprise a carbonaceous compound.

In accordance with yet another embodiment of the invention, the previously prepared particulate alkali metal carbonate catalyst support can be contacted with at least one elemental alkali metal to produce a catalyst composition.

In accordance with yet a further embodiment of the invention, the alkali metal carbonate catalyst support and the elemental alkali metal catalyst composition can be contacted with at least one promoter.

SUPPORTS

As used in this disclosure, the term "support" refers to a carrier for another catalytic component. However, by no means, is the support necessarily an inert material; it is possible that the support can contribute to catalytic activity and selectivity.

Commercially available alkali metal carbonate, in the form of powder, granules, or the like, is mixed with just enough alcohol to form a thick paste. In accordance with this invention, when forming the thick paste, at least a portion of the alcohol mixed with the alkali metal carbonate must be methanol ($CH_3OH$). Methanol is necessary in that methanol allows sufficient dissolution of the alkali metal carbonate to make a hard support, but not dissolution the extent of producing a non-porous support material. Additionally, methanol is advantageous because of relatively easy and rapid removal from the resultant support, due to its low boiling point.

Optionally, higher alcohols can be used in combination with the methanol to form the thick paste. As used in this disclosure, the term "higher alcohol" is defined as straight chain and branched aliphatic alcohols having from about 2 to about 7 carbon atoms per molecule. Suitable alcohols include, but are not limited to, ethanol, 1-propanol, 1-butanol, 1-pentanol, 1-hexane, 1-heptanol, 2-propanol, 2-butanol, 3-pentanol, 3-hexanol, 4-heptenol, isopropanol, isobutanol, tert-butanol, 2methyl-1-1-pentanol, 2-methyl-1-hexanol, 3-methanol-1-pentanol, 3-methyl-1-hexanol, 4-methyl-1-pentanol, 4-methyl-1-hexanol, 5-methyl-1-hexanol, 2-ethyl-1-pentanol, and the like, and mixtures thereof. Preferably, if the higher alcohol is combined with methanol, 1-propanol or isopropanol are used in the preparation of the alkali metal carbonate catalyst support material for best compatibility with methanol and alkali metal carbonate.

The thick paste usually comprises greater than or equal to about 80 weight percent dried alkali metal carbonate and less than or equal to about 20 wieght percent methanol or methanol/higher alcohol. More preferably, the thick paste comprises about 80 to about 90 weight percent dried alkali metal carbonate and about 20 to about 10 weight percent methanol or methanol/higher alcohol; most preferably, the thick paste comprises from about 82 to about 85 weight percent alkali metal carbonate and from about 18 to about 15 weight percent methanol or methanol/higher alcohol for ease of extrusion and a good, useable resultant catalyst support product. Generally, if larger quantities of the alkali metal carbonate support are prepared, less methanol or methanol/higher alcohol will be necessary.

Expressed in different, but comparable terms, the ratio of the mass of methanol or methanol/higher alcohol to the mass of dried alkali metal carbonate is usually less than about 0.25. Preferably, the ratio of the mass of methanol or methanol/higher alcohol to the mass of dried alkali metal carbonate is usually within the range of about 0.1 to about 0.25, and most preferably within the range of abut 0.17 to about 0.22 for reasons given above.

If a higher alcohol is combined with methanol, usually the methanol/alcohol mixture, also referred to as "alcohol mixture", will comprise at least about 50 percent by weight methanol. Preferably, the alcohol mixture will comprise at least about 70 percent by weight methanol, and most preferably from 80 to 99 weight percent methanol, for best compatibility with an alkali metal carbonate, as well as producing a more easily impregnatable support material.

Any alkali metal carbonate can be used in the preparation of the catalyst support. Exemplary compounds include, but are not limited to, sodium carbonate, potassium carbonate, and/or cesium carbonate. Preferably, sodium carbonate or potassium carbonate are used and most preferably, potassium carbonate is used for ease of use and, availability.

The alkali metal carbonate support can optionally contain at least one carbonaceous compound. The carbonaceous compound can be added simultaneously with the alkali metal carbonate and methanol or methanol/higher alcohol mixture. For purposes of this disclosure, the term "carbonaceous compound" is intended to include various forms of the element carbon, including, but not limited to carbon black, charcoal, coconut charcoal, amorphous graphite, crystallite graphite, and the like, as well as mixtures of any two or more thereof. Finely divided graphite is presently preferred because it is both useful as a die lubricant for pelleting and extrusion processes and it imparts improved activity to the finished dimerization catalyst system. The carbonaceous compound, if employed, comprises from about 0.01 to about 20 weight percent of the total alkali alkali metal carbonate support. Preferably, the carbonaceous compound comprises from about 0.1 to about 10 weight percent, and most preferably, the carbonaceous compound comprises about 0.3 to about 5 wieght percent of the alkali metal carbonate support material.

The thick paste can then be formed into a praticulate product prior to calcining. The paste can be formed into an extrudate using an extruder. The extrudate can be any diameter, but for best catalytic activity and ease of handling and processability, the extrudate is from about 1/16 to about ¼ inch in diameter. After the extrudate passes through the die, the extrudate can be cut into uniform lengths, if desired. However, uniform lengths are not always necessary, so the extrudate can be allowed to break on its own, into any length. If the extrudate is allowed to break on its own, it will usually have a length of about 2 to about 7 times the diameter width. Usually, the extrudate is allowed to break of its own accord because of ease of manufacture. Preferably, the particulate product is formed by extrusion for maximum efficiency and to produce a good, consistent quality catalyst support. The extrusion process results in a high yield of catalyst support product per given unit of time.

The thick paste after drying and granulation can also be formed into tablets using a die press, a punch press, or a pelleting machine. Tablets are usually very uniform in size. Tablets look similar to an extrudate, except tablets, generally, are more uniform in length and can have smooth, convex ends. Tablets can also have one or more holes through the tablet along the axis of the cylinder.

The thick paste can also be formed into pellets and/or pills. Pellets and pills can be defined as any other type of form that are not prepared using an extruder, a die press, punch press, or pelleting machine. One example of an apparatus used to make pellets or pills is a disk spherudizer. A disk spherudizer, or disk pelletizer, is a flat, circular disk with a lip perpendicularly attached around the circumference of the disk. The disk is mounted at an angle and rotates; scrapers are stationarily mounted above the disk. The disk rotating speed, angle of the disk, solids feed rate onto the disk, and ratio of liquids to solids all control the diameter of the pellets. Usually, the solids and liquids are not mixed prior to introduction onto the disk, but they can be pre-mixed.

Another method of forming a particulate product from the thick paste is to oven dry the thick paste under conditions of time and temperature sufficient to insure that substantially all of the alcohol has been driven off. The dried paste can then be broken into pieces and fractionated by suitable means such as, for example, by passing through the appropriate mesh size screen seives to recover a desired particle size fraction.

After formation of the extrudate, tablets, pellets, or pills, the catalyst support should be dried under conditions of time and temperature sufficient so that substantially all of the alcohol is driven off. Catalyst system supports prepared from alkali metal carbonate, methanol, and optionally, a higher alcoohol, can be more easily prepared than other catalyst system supports in that an alcohol-based support, after drying alone, has numerous pores and can be more easily impregnated with elemental alkali metal catalyst. A calcination step is not required with catalyst supports prepared from an alkali metal carbonate and alcohol. Catalyst system supports preapred from a thick paste of alkali methal carbonate and at least some water, have a thick "barrier" wall after drying and are more difficult to impregnate with elemental alkali metal catalyst. Thus, supports prepared from a water-containing thick paste must be calcined prior to impregnation, in order to fracture the "barrier" wall and create pores so that an elemental alkali metal catalyst can thoroughly impregnate the support. Usually, a drying temperature of at least 200° C., under ambient pressure, preferably at a temperature within the range of about 20° to about 50° C. for a time of at least 2 hours is sufficient. However, the drying temperature can be lowered if a vacuum or partial vacuum is used. Upon completion of calcination, the catalyst support can be stored in a dry atmosphere. Preferably, the catalyst support is stored under a dry, oxygen-free atmosphere until needed for further treatment.

CATALYST AND PROMOTERS

Catalyst systems employed in the practice of this invention comprise one of the alkali metal carbonate supports described above, at least one elemental alkali metal catalyst, and optionally one or more of the following additional promoters:
 elemental copper,
 elemetal cobalt,
 finely divided stainless steel,
 finely divided glass, and
 mixtures of two or more thereof.

It should be recognized, however, that the catalyst systems of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium, cesium, and mixtures thereof. While the proportion of alkali metal combines with the alkali metal carbonate support can vary appreciably, generally at least about one weight percent of alkali metal based on the total weight of treated support will be employed. Generally, about 1 to about 20 weight percent alkali metal will be employed with about 2 to about 15 weight percent preferred. An alkali metal loading of about 3 to about 10 weight percent based on the total weight of treated support is most preferred for most efficient use of reagents, high catalyst activity and selectivity, and ease of catalyst preparation. Potassium is the preferred elemental alkali metal due to its ready availability, ease and safety in handling, as well as high activity and product selectivity of the resultant catalyst system.

The proportion of optional promoter on the alkali metal carbonate support can vary appreciably, but generally, at least one weight percent of the optional promoter based on the total weight of treated support will be employed. The following amounts are provided for additional guidance:

| Promoter | Loading, Weight Percent | | |
|---|---|---|---|
| | Broad | Intermediate | Preferred |
| Cu | 1–30 | 3–20 | 5–12 |
| Co | 1–50 | 3–25 | 5–15 |
| *SS | 1–80 | 3–60 | 5–50 |
| Glass | 1–50 | 2–25 | 3–15 |

*SS = Stainless Steel

The general procedure for preparation of the catalyst systems, after calcining the support, of the invention involves heating the alkali metal carbonate support to a temperature in the range of about 80° to about 350° C., preferably slightly above the melting point of the particular alkali metal used, cooling the particulate support and then contacting the particulate support with at least one elemental alkali metal in a dry, oxygen-free atmosphere, such as, for example $N_2$, Ar, or the like, at a temperature sufficient to cause the alkali metal to melt. The contacting, done in an oxygen-free atmosphere, is preferably carried out with suitable mixing to ensure even distribution. Suitable temperatures for the contacting step will vary with the particular alkali metal employed. For example, with elemental potassium, temperatures in the range of about 80° to 100° C. are preferred, while with elemental sodium, temperatures in the range of about 100° to 140° C. are preferred.

While the alkali metal treated support is maintained at or above the melting point of the particular alkali metal used, in an oxygen-free atmosphere, any desired promoter(s), such as for example, finely divided stainless steel or elemental copper, can be gradually added while the treated catalyst is continuously stirred. For example, with potassium, temperatures in the range of about 80° to about 100° C. are employed. The catalyst system is then ready to be charged to the reactor.

Optionally, the alkali metal carbonate support, once elemental alkali metal and any desired promoters have been deposited thereon, can be subjected to a subsequent heating step, in an oxygen-free atmosphere, to ensure as uniform a distribution as possible of the various promoters on the surface of the alkali metal carbonate support. Thus, the finished catalyst can be subjected to a temperature in the range of at least about 80° C. for a time in the range of abut 0.1 to 4 hours. A temperature in the range of about 150° to about 250° C. for a time in the range of about 0.5–2 hours is presently preferred for the most uniform distribution.

Optionally, prior to charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance is glass beads.

As indicated by the variety of supports, alkali metal components, and promoters included within the scope of the invention, numerous catalyst combinations are possible. Any combination of the alkali metal and optional promoters disclosed can be supported on any alkali metal carbonate support disclosed. Some possible combinations are described in detail in the examples which follow. The combination of support, alkali metal and promoter(s) which one may choose to employ will depend on a variety of variables such as for example, reactor configuration, reaction temperature and pressure, olefin feed employed, rate of olefin feed, and conversions desired.

REACTANTS

Reactants applicable for use in the process of the invention are oleifinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimmerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as definde above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to acyclic and cyclic olefins such as for example propylene, 1-butene, 2-butene, isobutylene, 1-pentene, 2-pentene, 1-hexane, 2-hexane, 3-hexane, 1- heptene, 2-heptene, 3-heptene, the four normal octenes, the four normal nonenes and so forth; 3-methyl-1-butene, 2-methyl-2-butene, 3-methyl-1-pentene, 4-methyl-1-pentene, 4-methyl-2-pentene, tetramethylethylene and the like; cyclopentene, cyclohexene, methylcyclopentene, methylcyclohexene, and the like; cyclopentene, cyclohexene, methylcyclopentene, methylcyclohexene and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of the co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The do-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefor not capable of reacting with themselves under the reacton conditions employed for the dimerization reaction.

REACTION CONDITIONS

The dimerization reaction of the invention can be carried out using either batch or continuous types of operation, although the cataylsts of the invention are particularly well suited for continuous, fixed bed, operation. Suitable equipment such as for example autoclaves, tubular reactors and the like as are well known in the art can be employed. No special materials of construction are required so that steel, stainless steel, glass-lined reactors, or the like can be employed.

The reaction temperatue can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressure of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecaine; aromatic compounds preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitorgen, argon, can be present.

The contact time required for the dimerization reaction depends upon several factors such as for example the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant-catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

PRODUCTS

The olefinic products of the invention have established utility in a wide vcariety of applications such as for example as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLES

Example I

Extruded catalyst support was prepared from commercially available, anhydrous potassium carbonate (JT Baker, ACS agent grade) and methanol (ACS reagnet grade). Methanol was mixed with potassium carbonate, particle size of equal to or less than about 0.42 mm (40 mesh), to form a wet paste. The thick paste was throughly mixed and extruded through a die plate with ⅛ inch openings in a single screw, one (1) inch Bonnot extruder. The amount of methanol and number of die holes were varied to produce an extrudate. However, other methanol/potassium carbonate ratios can work at other die pressures, i.e., other numbers od die holes. Runs 106–109, of Table I, were extruded through a die with two (2) ⅛ inch die holes. Runs 101–105 and 110 of Table I, used a die with three (3) ⅛ inch die holes. Extrudate was collected and allowed to break into pieces; each piece was from about ¼ to about ⅞ inches long.

For comparative purposes, all extrudates were dried and clacined. The extrudate was dried at 150° C. in a vacuum oven for 3hours. The dried extrudate was then calcined for 3 hours in an oxygen-containing atmosphere at a temperature of at least about 270° C. and transferred to a dry, oxygen-free atmosphere. The resultant support was maintained at a temperature of about 80° to about 85° C., in an oxygen-free atmosphere, at which time 4 wieght percent of elemental potassium, based on the weight of the support, were added. At all times after calcination, the catalyst supports and catalyst systems were kept under a dry, inert atmosphere.

Results are summarized in Table I.

TABLE I

| Run | gMeOH/ gK2CO3 | Weight % MeOH[a] | Result | Observed Physical Characteristics |
| --- | --- | --- | --- | --- |
| 101 | 0.35 | 26 | Paste was too wet. | — |
| 102 | 0.16 | 14 | Extruded, but shut down the extruder after about ⅓ of the material was fed. Probably slightly too dry. | — |

TABLE I-continued

| Run | gMeOH/ gK2CO3 | Weight % MeOH[a] | Result | Observed Physical Characteristics |
|---|---|---|---|---|
| 103 | 0.18 | 15 | Extruded, but shut down the extruder after about ⅓ of the material was fed. Probably slightly too dry. | — |
| 104 | 0.22 | 18 | Extruded, but shut down the extruder after a small amount of the material was fed. | — |
| 105 | 0.26 | 21 | Mixture too wet to extrude. | — |
| 106 | 0.18 | 15 | Extruded using 2 hole instead of 3 hole die. Similar problem as with Run 103. | — |
| 107 | 0.18 | 15 | Used 2 hole cooled die and cooling jacket on extruder. Was able to extrude the mix. | — |
| 108 | 0.20 | 17 | Extruded | Network of small, fused, individual $K_2CO_3$ particles. Numerous small pores. |
| 109 | 0.19 | 16 | Extruded | Network of small, fused, individual $K_2CO_3$ particles. Numerous small pores. |
| 110 | 0.27[b] | 21 | Extruded | Large, fused $K_2CO_3$ globules, with thick barrier walls. Few large pores. |

[a]Based on weight of thick paste (e.g., weight dried $K_2CO_3$ plus weight MeOH)
[b]Water, instead of methanol, was used to make a $K_2CO_3$ wet paste.

Electron microscope examination showed differences between the extrudates that were extruded with methanol only, Runs 108 and 109, and a water-based extrudate, Run 110. Electron microscope examination showed that the catalyst prepared in Runs 108 and 109, methanol-based extrudates, had a network of small, fused individual potassium carbonate particles, whereas the catalyst support prepared in Run 110, a water-based extrudate, had large, fused potassium carbonate globules with thick barrier walls. The surface and interior of the methanol prepared extrudates (Runs 108 and 109) had numerous small pores, whereas the water extruded material (Run 110) had only a very low number of large pores. While not wishing to be found by theory, the more accessible, i.e., porous, catalyst support interior of the methanol/potassium carbonate extrusion can provide a better support for a dimerization catalyst system, such as for example, the dimerization of propylene to 4MP1. Furthermore, other methods for adjusting the potassium carbonate solubility can provide improved supports.

The results demonstrate that potassium carbonate supports for dimerization catalyst systems can be prepared by extruding potassium carbonate in methanol. The differences in porosity, apparent between alcohol-based extrudates (Runs 108 and 109) and water-based extrudate (Run 110), show that the resultant catalyst support is a new and distinct material.

Example II

The catalyst systems prepared in Example I were used to catalyze the dimerization of propylene to 4MP1. The dimerization of propylene was carried out in a steam heated 316 stainless steel tubular reactor (⅜"×20"). The catayslt system (27 grams; density about 0.84 g/mL), bounded above and below by small volumes of glass beads, was combined with 25 grams of an inert substance, i.e., no dimerization catalytic activity, to dilute the catalyst system and thus reduce and control the reaction rate. The contents of the tubular reactor were heated to the reaction temperature of about 160° C. at about 1500 psig and propylene was pumped into the reactor at a rate of about 120 mL/hr. After about 1.5 hours of reaction time and each one hour thereafter for the following 6 hours, a sample was collected and analyzed by gas liquid chromatography (glc).

The summarized results are given in Table II. Propylene conversion, percent, as used in Table II, is the weight percent of reactant propylene that was converted to any type of reaction product. Selectivity, percent, is the weight percent of product that was 4-methyl-1-pentene (4MP1).The isomer ratio, 4-methyl-1-pentene/4-methyl-2-pentene (4MP1/4MP2), is the weight ratio of 4MP1/4MP2 in the final product. The isomer ratio data is significant because 4MP1 and 4MP2 are difficult to separate.

TABLE II

| Time, hr | Runs 108–110 Propylene Conversion, % | | | Runs 108–110 4MP1 Selectivity, % | | | Runs 108–110 4MP1/4MP2 ratio | | |
|---|---|---|---|---|---|---|---|---|---|
| Run | 108 | 109 | 110 | 108 | 109 | 110 | 108 | 109 | 110 |
| 0 | 0 | 0 | 0 | 0 | 0 | 0 | 0 | 0 | 0 |
| 2 | 13.4 | 0.9 | 1.1 | 67.2 | 80.6 | 49.1 | 2.6 | 6.3 | 1.5 |
| 3 | 21.0 | 14.6 | 8.9 | 69.4 | 70.8 | 87.7 | 2.8 | 3.3 | 20.0 |
| 4 | 26.8 | 12.3 | 22.1 | 72.3 | 73.0 | 89.1 | 3.3 | 3.5 | 22.0 |
| 5 | 23.8 | 18.1 | 25.7 | 82.3 | 78.1 | 89.0 | 7.6 | 4.9 | 21.9 |
| 6 | 21.8 | 22.9 | 24.9 | 85.1 | 85.0 | 89.1 | 9.2 | 9.2 | 22.3 |
| 7 | 22.0 | — | 25.3 | 86.6 | — | 89.2 | 11.3 | — | 22.6 |
| 7.5 | — | 24.5 | — | — | 88.1 | — | — | 14.6 | — |
| 8 | — | — | 26.9 | — | — | 89.1 | — | — | 22.4 |
| 8.5 | — | 37.1 | — | — | 88.0 | — | — | 14.5 | — |
| 9 | — | — | 27.9 | — | — | 89.1 | — | — | 22.1 |
| 9.5 | — | 25.0 | — | — | 88.1 | — | — | 14.5 | — |
| 10.5 | 20.2 | 27.6 | 28.9 | 89.0 | 88.0 | 89.0 | 17.1 | 14.4 | 21.9 |
| 11.5 | 24.4 | 28.6 | — | 88.7 | 89.3 | — | 15.9 | 18.5 | — |
| 12.5 | 24.8 | 25.5 | 29.6 | 88.6 | 89.1 | 89.7 | 15.8 | 17.7 | 26.5 |
| 13.5 | 20.4 | — | 29.9 | 89.0 | — | 89.5 | 17.2 | — | 26.0 |
| 14 | 21.0 | — | — | 89.0 | — | — | 17.0 | — | — |
| 14.5 | — | 28.9 | 32.1 | — | 89.0 | 89.5 | — | 17.5 | 25.1 |

TABLE II-continued

| Time, hr | Runs 108-110 Propylene Conversion, % | | | Runs 108-110 4MP1 Selectivity, % | | | Runs 108-110 4MP1/4MP2 ratio | | |
| --- | --- | --- | --- | --- | --- | --- | --- | --- | --- |
| Run | 108 | 109 | 110 | 108 | 109 | 110 | 108 | 109 | 110 |
| 15 | 21.1 | — | — | 89.0 | — | — | 17.0 | — | — |
| 15.5 | — | 28.9 | 29.8 | — | 88.7 | 89.6 | — | 17.5 | 26.0 |
| 16 | 21.6 | — | — | 89.1 | — | — | 17.0 | — | — |
| 16.5 | — | 28.6 | 29.5 | — | 89.3 | 89.7 | — | 18.0 | 26.2 |
| 17 | 21.7 | — | — | 89.2 | — | — | 17.2 | — | — |

As shown in Table II, the methanol extruded samples, Runs 108 and 109, show a longer induction period for reaching stable selectivities and 4MP1/4MP2 ratios. Runs 108 and 109 also result in lower 4MP1/4MP2 ratios than does Run 110. These results suggest that catalyst supports, prepared from an alcohol-based extrudate (Runs 108 and 109), behave differently from catalyst supports prepared from a water-based extrudate (Run 110). It is possible that optimization of the potassium loading for these materials, as well as the support preparation conditions, could give improved performance.

The data, however, demonstrate that 1) alcohol-based, i.e., methanol, extruded supports are useful as catalyst system supports and 2) based on induction time and 4MP1/4MP 2 ratios, alcohol-based extruded supports are difference from water-based extruded supports.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for the preparation of a catalyst support consisting essentially of:
   (a) preparing a thick paste consisting essentially of an alkali metal carbonate and methanol;
   (b) forming a particulate product from said paste; and
   (c) drying said particulate product.

2. A process according to claim 1 wherein said alkali metal carbonate is selected from the group consisting of sodium carbonate, potassium carbonate, and cesium carbonate.

3. A process in accordance with claim 1 wherein said thick paste further consists essentially of a carbonaceous compound.

4. A process in accordance with claim 1 wherein said thick paste further consists essentially of a higher alcohol.

5. A process according to claim 4 wherein said higher alcohol is an aliphatic alcohol containing from about 2 to about 7 carbon atoms per molecule.

6. A process according to claim 4 wherein said higher alcohol is selected from the group consisting of 1-propanol, iso-propanol, and mixtures thereof.

7. A process in accordance with claim 1 wherein said thick paste consists essentially of greater than or equal to about 80 weight percent dried alkali metal carbonate and less than or equal to about 20 weight percent alcohol.

8. A process in accordance to claim 1 wherein said particulate product is formed by;
   (a) extruding said thick paste to form an extrudate; and
   (b) drying the extrudate of step (a) under conditions suitable to remove essentially all alcohol from said extrudate.

9. A process for producing a catalyst system which consists essentially of contacting a catalyst support prepared in accordance with claim 1 with at least 1 elemental alkali metal in an oxygen-free atmosphere at a temperature sufficient to cause the alkali metal to melt.

10. A process according to claim 9 further consisting essentially of contacting said catalyst system with a promoter selected from the group consisting of finely divided stainless steel, elemental copper, elemental cobalt, finely divided glass, and mixtures thereof.

11. A process according to claim 9 wherein said elemental alkali metal is potassium.

12. A process according to claim 9 wherein said elemental alkali metal consists essentially of from about 1 to about 20 weight percent of said catalyst system.

13. A catalyst produced by the process of claim 9.

14. A catalyst produced by the process of claim 10.

15. A process for the preparation of a catalyst support consisting essentially of:
   (a) preparaing a thick paste consisting essentially of an alkali metal carbonate and methanol;
   (b) forming a particulate product from said paste; and
   (c) drying said particulate product at a temperature of less than about 200° C.

16. A process according to claim 15 wherein said drying temperature is less than about 50° C.

* * * * *